US00PP34565P2

(12) United States Plant Patent
Koene

(10) Patent No.: US PP34,565 P2
(45) Date of Patent: Sep. 13, 2022

(54) ***MANDEVILLA* PLANT NAMED 'SUNPA 201'**

(50) Latin Name: *Mandevilla hybrida*
Varietal Denomination: Sunpa 201

(71) Applicant: Tim Koene, Maasland (NL)

(72) Inventor: Tim Koene, Maasland (NL)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 17/571,471

(22) Filed: Jan. 8, 2022

(51) Int. Cl.
*A01H 6/08* (2018.01)
*A01H 5/02* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. Anne Whealy

(57) ABSTRACT

A new and distinct cultivar of *Mandevilla* plant named 'Sunpa 201', characterized by its upright to outwardly spreading plant habit; vigorous growth habit; freely branching habit; early and freely flowering habit; long flowering period; and medium-sized speckled red and light purplish pink bi-colored flowers with light purplish pink-colored petal margins.

1 Drawing Sheet

Figure 1:
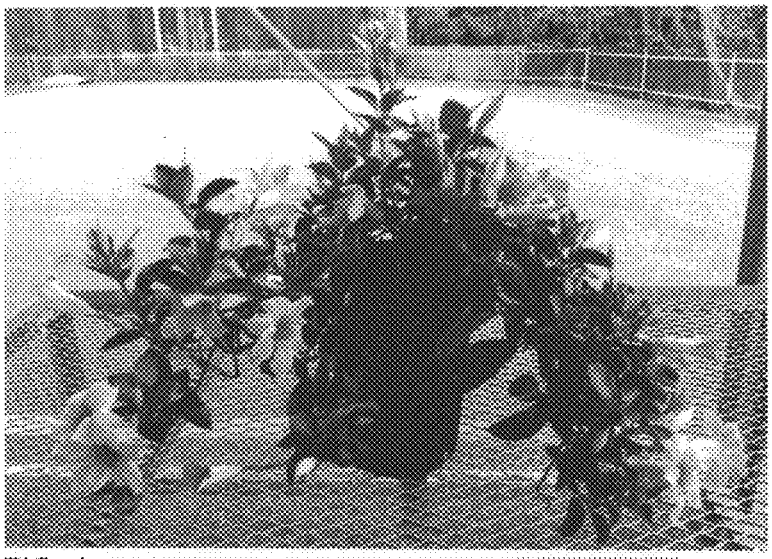

Botanical designation: *Mandevilla hybrida.*
Cultivar denomination: 'SUNPA 201'.

STATEMENT REGARDING PRIOR DISCLOSURES BY THE INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla hybrida* and hereinafter referred to by the name 'Sunpa 201'.

The new *Mandevilla* plant is a naturally-occurring whole plant mutation of a proprietary selection of *Mandevilla hybrida* identified as code number M37-mt2, not patented. The new *Mandevilla* plant was discovered and selected by the Inventor as a single flowering plant from within a population of plants of the mutation parent selection in a controlled greenhouse environment in Maasland, The Netherlands in June, 2019.

Asexual reproduction of the new *Mandevilla* plant by terminal vegetative cuttings in Maasland, The Netherlands since June, 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 201'. These characteristics in combination distinguish 'Sunpa 201' as a new and distinct *Mandevilla* plant:

1. Upright to outwardly spreading plant habit.
2. Vigorous growth habit.
3. Freely branching habit.
4. Early and freely flowering habit.
5. Long flowering period.
6. Medium-sized speckled red and light purplish pink bi-colored flowers with light purplish pink-colored petal margins.

Plants of the new *Mandevilla* can be compared to plants of the mutation parent selection. Plants of the new *Mandevilla* differ primarily from plants of the mutation parent selection in flower color as plants of the new *Mandevilla* have speckled red and light purplish pink bi-colored flowers whereas plants of the mutation parent selection have light purplish pink-colored flowers.

Plants of the new *Mandevilla* can be compared to plants of the *Mandevilla hybrida* 'Sunpa 4411', disclosed in U.S. Plant Pat. No. 31,141. In side-by-side comparisons, plants of the new *Mandevilla* differ from plants of 'Sunpa 4411' in the following characteristics:

1. Plants of the new *Mandevilla* have shorter internodes than plants of 'Sunpa 4411'.
2. Leaves of plants of the new *Mandevilla* are smaller than leaves of plants of 'Sunpa 4411'.
3. Petals of plants of the new *Mandevilla* are imbricate whereas petals of plants of 'Sunpa 4411' are not imbricate.
4. Plants of the new *Mandevilla* have speckled red and light purplish pink bi-colored flowers whereas plants of 'Sunpa 4411' have purplish red-colored flowers.

5. Plants of the new *Mandevilla* have shorter peduncles than plants of 'Sunpa 4411'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet (FIG. 1) is a side perspective view of a typical flowering plant of 'Sunpa 201' grown in a container.

Figure 2:
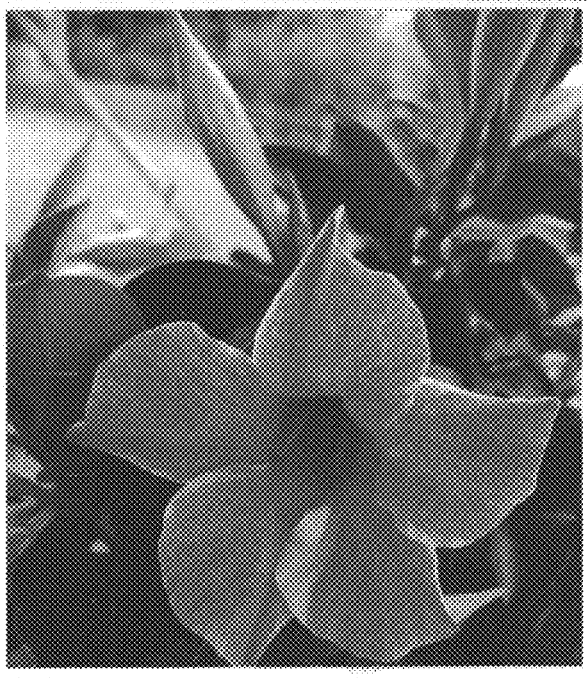

The photograph at the bottom of the sheet (FIG. 2) is a close-up view of a typical flower and flower buds of 'Sunpa 201'.

DETAILED BOTANICAL DESCRIPTION

The aforementioned photographs and following observations, measurements and values describe plants grown during the early autumn in 18-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 201'.

Parentage: Naturally-occurring whole plant mutation of a proprietary selection of *Mandevilla hybrida* identified as code number M37-mt2, not patented.

Propagation:

*Type.*—By terminal vegetative cuttings.

*Time to initiate roots, summer and winter.*—About two weeks at temperatures about 23° C. to 25° C.

*Time to produce a rooted young plant, summer and winter.*—About five to six weeks at temperatures about 23° C. to 25° C.

*Root description.*—Fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading plant habit; vigorous growth habit; freely branching habit with about five primary lateral branches; suitable for hanging baskets and garden plantings.

*Plant height.*—About 32 cm.

*Plant diameter.*—About 75 cm.

*Lateral branch description.*—Length: About 2.3 cm. Diameter: About 3.5 mm. Internode length: About 3.3 cm. Strength: Strong, flexible. Texture: Smooth, glabrous. Color, developing: Close to 143A. Color, fully developed: Close to N199A.

Leaf description:

*Arrangement.*—Decussate, simple.

*Length.*—About 5.5 cm.

*Width.*—About 3.8 cm.

*Shape.*—Ovate.

*Apex.*—Acuminate.

*Base.*—Cordate.

*Margin.*—Entire; moderately undulate and incurving.

*Texture and luster, upper and lower surfaces.*—Smooth, glabrous; semi-glossy.

*Venation pattern.*—Pinnate, reticulate.

*Color.*—Developing leaves, upper surface: Close to 137B. Developing leaves, lower surface: Close to 138B. Fully expanded leaves, upper surface: Close to 139A; venation, close to 143A. Fully expanded leaves, lower surface: Close to 146A; venation, close to 146D.

*Petioles.*—Length: About 1.1 cm. Diameter: About 1.7 mm. Texture, upper and lower surfaces: Smooth, glabrous. Color, upper and lower surfaces: Close to 137C.

Flower description:

*Flower type and habit.*—Single salverform flowers; flowers face upright to outwardly; freely flowering habit with about three to five flowers per axil and about 65 flowers developing per plant.

*Natural flowering season.*—Early flowering habit, plants begin flowering about six weeks after planting rooted cuttings; long flowering period, plants flower continuously from summer until late autumn in Japan.

*Flower longevity on the plant.*—About seven to ten days; flowers not persistent.

*Fragrance.*—None detected.

*Flower buds.*—Height: About 7 cm. Diameter: About 1.5 cm. Shape: Rhombic. Color: Proximally, close to 45A and distally, close to 63B.

*Flowers.*—Appearance: Salverform; flared trumpet, corolla fused and five-parted; flowers roughly star-shaped. Diameter: About 7.4 cm. Depth (length): About 6.5 cm. Throat diameter: About 1.9 cm. Tube length: About 1.8 cm. Tube diameter, proximally: About 4.1 mm.

*Corolla.*—Quantity and arrangement: Five petals arranged in a single whorl and fused towards the base into an elongated tube; petal lobes imbricate. Petal lobe length: About 3.2 cm. Petal lobe width: About 2.7 cm. Petal lobe shape: Spatulate, asymmetrical. Petal lobe apex: Acuminate. Petal lobe margin: Entire; moderately undulate and slightly recurved. Petal lobe texture and luster, upper and lower surfaces: Smooth, glabrous; velvety; matte. Throat texture and luster: Smooth, glabrous; matte. Tube texture and luster: Smooth, glabrous; matte. Color: Petal lobe, when opening, upper surface: Close to 60A and 62B, speckled. Petal lobe, when opening, lower surface: Close to 63A and 62D, speckled. Petal lobe, fully opened, upper surface: Close to 53B and 62C, speckled; edges, close to 62C; venation, similar to lamina; color becoming closer to 61C with subsequent development. Petal lobe, fully opened, lower surface: Close to 67A and 63D, speckled; venation, similar to lamina; color does not change with subsequent development. Throat: Proximally, close to N25B and 71A with suture, close to 75D; distally, close to 32A and 175B; suture, close to 163A. Tube: Close to 63B and 62D; distally, close to 45B and 145C.

*Calyx.*—Quantity and arrangement: Five sepals arranged in a single whorl, fused at the base; calyx, star-shaped. Sepal length: About 6.8 mm. Sepal width: About 2.3 mm. Sepal shape: Lanceolate. Sepal apex: Acute. Sepal margin: Entire. Sepal texture, upper and lower surfaces: Smooth, glabrous. Sepal color, upper surface: Close to 144A; towards the apex, close to 64A. Sepal color, lower surface: Proximally, close to 145A and distally, close to 142A variably tinged with close to 71C.

*Peduncles.*—Length: About 2.2 cm. Diameter: About 3.6 mm. Texture: Smooth, glabrous. Aspect: Upright to outwardly. Color: Close to 144B.

*Pedicels.*—Length: About 1.6 cm. Diameter: About 2.3 mm. Texture: Smooth, glabrous. Aspect: Upright to outwardly. Color: Close to 145A variably tinged with close to 64A.

*Reproductive organs.*—Stamens: Quantity and arrangement: Typically five; filaments fused to corolla; anthers, connivent. Anther size: About 1.5 mm by 8.7 mm. Anther shape: Lanceolate. Anther color: Close to 160C. Pollen amount: None observed. Pistils: Quantity: Typically one. Pistil length: About 2.6 cm. Style color: Close to 145D. Stigma shape: Conical. Stigma color: Close to 143B. Ovary color: Close to 144A.

*Seeds and fruits.*—To date, seed and fruit production have not been observed on plants of the new *Mandevilla.*

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 201' as illustrated and described.

* * * * *